US007604645B2

(12) United States Patent
Barzell et al.

(10) Patent No.: US 7,604,645 B2

(45) Date of Patent: Oct. 20, 2009

(54) ULTRASOUND PROBE SUPPORT AND STEPPING DEVICE

(75) Inventors: Winston E. Barzell, Sarasota, FL (US); Willet F. Whitmore, Sarasota, FL (US); Stephen E. Brauner, Bradenton, FL (US); Roger Wilson, Sarasota, FL (US)

(73) Assignee: CIVCO Medical Instruments Inc., Kalona, IA (US)

( * ) Notice: Subject to any disclaimer, the term of this patent is extended or adjusted under 35 U.S.C. 154(b) by 91 days.

(21) Appl. No.: 10/636,456

(22) Filed: Aug. 7, 2003

(65) Prior Publication Data

US 2004/0143188 A1 Jul. 22, 2004

Related U.S. Application Data

(60) Provisional application No. 60/401,830, filed on Aug. 7, 2002.

(51) Int. Cl.
*A61B 19/00* (2006.01)

(52) U.S. Cl. ....................... 606/130; 600/429; 600/459; 600/439; 600/437

(58) Field of Classification Search ................. 600/459, 600/562, 439; 606/130
See application file for complete search history.

(56) References Cited

U.S. PATENT DOCUMENTS

| | | | | |
|---|---|---|---|---|
| D271,136 | S | 10/1983 | Bollinger et al. | D24/17 |
| 4,543,649 | A | 9/1985 | Head et al. | 367/96 |
| 4,694,230 | A | 9/1987 | Slocum et al. | 318/568 |
| 4,742,829 | A | 5/1988 | Law et al. | 128/660 |
| 4,767,406 | A | 8/1988 | Wadham et al. | 604/155 |
| 5,178,148 | A | 1/1993 | Lacoste et al. | 128/660.03 |
| 5,184,601 | A | 2/1993 | Putman | 128/4 |
| 5,398,690 | A | 3/1995 | Batten et al. | 128/662.05 |
| 5,474,071 | A | 12/1995 | Chapelon et al. | 128/660.03 |
| 5,494,039 | A | 2/1996 | Onik et al. | 128/662.05 |
| 5,592,942 | A | 1/1997 | Webler et al. | 128/660.09 |
| 5,695,500 | A | 12/1997 | Taylor et al. | 606/130 |
| 5,695,501 | A | 12/1997 | Carol et al. | 606/130 |
| 5,697,939 | A | 12/1997 | Kubota et al. | 606/130 |
| 5,871,448 | A * | 2/1999 | Ellard | 600/459 |
| 5,931,786 | A | 8/1999 | Whitmore, III et al. | 600/459 |
| 5,938,583 | A | 8/1999 | Grimm | 600/7 |

(Continued)

OTHER PUBLICATIONS

B & K User Guide for the Stepping Unit UA 1084 (Oct. 1994).

(Continued)

*Primary Examiner*—Brian Casler
*Assistant Examiner*—John F Ramirez
(74) *Attorney, Agent, or Firm*—Steptoe & Johnson LLP

(57) ABSTRACT

The present invention provides an apparatus for guiding a medical instrument. The medical apparatus includes a bracket member having a cavity dimensioned and configured to receive at least a portion of a medical instrument. A carriage member is slidably connected to a base assembly adapted to move the carriage member into an imaging position. The carriage assembly is adapted to rotationally support the bracket member, as well as provide a vertically adjustable height of the bracket member. A quick release member is operatively associated with the bracket and carriage members for removably attaching and detaching the bracket member to and from the carriage member when the carriage member is in the imaging position without losing the position and orientation of the carriage member.

19 Claims, 11 Drawing Sheets

U.S. PATENT DOCUMENTS

| | | | | |
|---|---|---|---|---|
| 5,961,527 | A | 10/1999 | Whitmore, III et al. | 606/130 |
| 6,007,474 | A | 12/1999 | Rydell | 600/7 |
| 6,206,832 | B1 | 3/2001 | Downey et al. | 600/439 |
| 6,248,101 | B1 | 6/2001 | Whitmore, III et al. | 606/1 |
| 6,292,681 | B1 | 9/2001 | Moore | 600/407 |
| 6,554,759 | B2 * | 4/2003 | Fontayne et al. | 600/7 |
| 6,659,956 | B2 | 12/2003 | Barzell et al. | 600/461 |
| 2003/0199785 | A1 * | 10/2003 | Hibner et al. | 600/562 |

OTHER PUBLICATIONS

"Martin" Immobilization Device, Catalog #9102-MA, Mick Radio-Nuclear Instruments, Inc., 4 pages (1996/1998).
Northwest Transperineal Prostate Implant Stabilization Device, Transperineal Prostate Implant Dosimetry Service, 2 pages (1996).
"Cotan Stabilizing Device," Catalog #8812-C, Mick Radio-Nuclear Instruments, Inc., 4 pages (1996/1998).
"Portable Stabilizes," Hutchinson Medical Designs, 1 page.
"A.2 Fixation Unit UA1116"; Geninfo, 5 pgs., May 1996.
"Hawk" and "Falcon" Brachytherapy Stabilizers; Wave Form Systems; 2 pages, 1998.
"ProScan® plus"; Brachytherapy Seed Guide and Probe Holder, 3 pages.
"Brachytherapy," Carolina Medical Inc., 4 pages.
CIVCO Medical Instruments Co., Inc. Transducer Covers. Biopsy Needle Guides. GE Medical Systems Imaging Accessories—vol. 1, pp. cover, 10-11, back cover, dated 2003.
CIVCO Medical Instruments Imaging Supplies vol. 1, pp. cover, 1, 24, 26-28, back cover, dated 2003.

* cited by examiner 210
242
226
218
38
40

ULTRASOUND PROBE SUPPORT AND STEPPING DEVICE

CROSS-REFERENCE TO RELATED APPLICATION

This application claims the benefit under 35 U.S.C § 119 (e) of U.S. Provisional Patent Application No. 60/401,830, filed Aug. 7, 2002, entitled ULTRASOUND PROBE SUPPORT AND STEPPING DEVICE, the entirety of which is incorporated herein by reference.

FIELD OF THE INVENTION

This invention relates generally to support apparatus for precision medical instruments, and more particularly to an adjustable support and stepping device for use with transrectal ultrasound imaging probes and a template grid or matrix.

BACKGROUND OF THE INVENTION

Brachytherapy (radioactive seeds), thermotherapy (heating), and cryotherapy (freezing) are proven therapies for tumors, both benign and malignant. Although the effectiveness of these treatments has been established, the risks associated with these treatments prevent or at least inhibit the wide application that they might otherwise achieve. The risks in each instance are related to the difficulties in achieving full control and accurate monitoring of the treatment. The risks of damaging surrounding tissues are present in every case, potentially catastrophic and require great care and experience to control.

In this regard, these therapies are frequently performed in conjunction with an ultrasound imaging probe placed in the rectum to monitor treatment. A template grid arrangement, which is kept in precise linear orientation with the ultrasound probe, must be accurately oriented adjacent the perineum in relation to the prostate, and locked in position throughout the procedure to achieve optimum results. Precise and reproducible orientation and positioning of the ultrasound imaging probe in the rectum is a key element in the clinical application of these therapies.

A number of prior art devices provide the necessary orientation and positioning. For example, U.S. Pat. No. 5,931,786, the contents of which are incorporated herein by reference, discloses a template grid support or mount and an ultrasound probe support (collectively referred to as a stepper) with a stepping function for precision axial longitudinal movement and rotation of an ultrasound probe. During a procedure, the ultrasound probe is manually inserted into the rectum and, once the desired orientation is achieved as viewed and confirmed by the monitored ultrasound images, the probe is connected to the stepper (which is typically attached to a support stand). Alternatively, if the support stand has suitable mobility, the stepper and probe can be attached to the support stand before insertion into the rectum. With the support stand set in a fixed mode, a range of positively controlled microadjustments may be used to achieve an ideal probe or instrument orientation for starting the procedure.

The template grid mount supports a needle guiding template grid which may be moved longitudinally along the centerline axis of the ultrasound probe while keeping a constant radial distance from this same axis. The stepping function allows precise, independent, and reproducible longitudinal movement of the ultrasound probe while keeping it in accurate radial position in relation to the grid. The rotation function of the stepper permits free axial rotation of the ultrasound probe and easy placement and removal of the ultrasound probe from the stepping device while retaining position of the stepping function and the template grid.

Thus, the stepper allows rotation and longitudinal movement along the axis of the ultrasound probe. However, no vertical adjustments of the ultrasound probe with respect to template grid is possible. Such vertical adjustments could be advantageous for improving treatment efficacy and safety. As previously noted, the major concern and risk of morbidity from cryotherapy and thermotherapy is thermal damage to the rectal area. This worry often limits effective treatment at the posterior margins of the prostate. In the case of cryotherapy, freezing this area is required and if the freezing is too aggressive a postoperative fistula from the prostate to the rectum may result from also freezing the rectal wall.

These concerns have been dealt with clinically by using a number of techniques to reduce pressure on the anterior rectal wall, thereby improving blood flow and decreasing the chances of freezing this vital area: removing the ultrasound probe during freezing or; placing weights on the probe to pull it posteriorly away from the anterior rectal wall during freezing. The latter technique is preferred because it maintains some ultrasound visibility. These techniques may be enhanced by injecting warm saline into the rectum during freezing of the prostate or by injecting fluid in the potential space between the posterior prostate and anterior rectal wall to create additional separation prior to freezing the prostate. However, all these current methods for improving safety require actively moving the ultrasound probe away from the anterior rectal wall using methods that are clumsy, time consuming and that significantly compromise good visibility using the ultrasound image. The proposed invention described herein provides a convenient, controlled and safe method for moving the ultrasound probe away from the anterior rectal wall when desired with minimal compromise of the ultrasound images and no disruption of the surgical field, as well as exact restoration of the initial imaging position at the completion of the freezing cycle.

As the previous discussion illustrates, a need for an improved stepper exists.

SUMMARY OF THE INVENTION

The present invention provides a medical apparatus for guiding a medical instrument. The medical apparatus includes a base assembly having a carriage assembly slidingly mounted thereto. The carriage assembly is adapted to controllably transverse the base assembly, moving the carriage assembly into an image position.

A medical instrument mount is rotatably mounted to the carriage assembly, wherein the medical instrument mount is configured to receive a medical instrument. Additionally, the medical instrument mount is mounted to the carriage assembly, such that the height of the medical instrument mount is adjustable on the carriage assembly. The rotatable mounting of the medical instrument mounts enables the medical instrument to be rotated about it longitudinal axis, without have to adjust the positions of the carriage assembly or the medical instrument mount.

A quick release member is operatively associated with the medical instrument mount and carriage assembly. The quick release member enables the medical instrument mount to be quickly and easily mounted to and removed from the carriage assembly when the carriage assembly is in the imaging position without losing position and orientation of the carriage assembly. The quick release member includes a grooved portion of the carriage assembly and a tongued portion of the medical instrument mount, the grooved portion configured and dimensioned to receive the tongued portion and the tongued portion releasable from the grooved portion by rotation of the medical instrument mount with respect to the carriage assembly.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

In the description which follows, any reference to either direction or orientation is intended primarily and solely for purposes of illustration and is not intended in any way as a limitation to the scope of the present invention. Also, the particular embodiments described herein, although being preferred, are not to be considered as limiting of the present invention.

Figure 1:
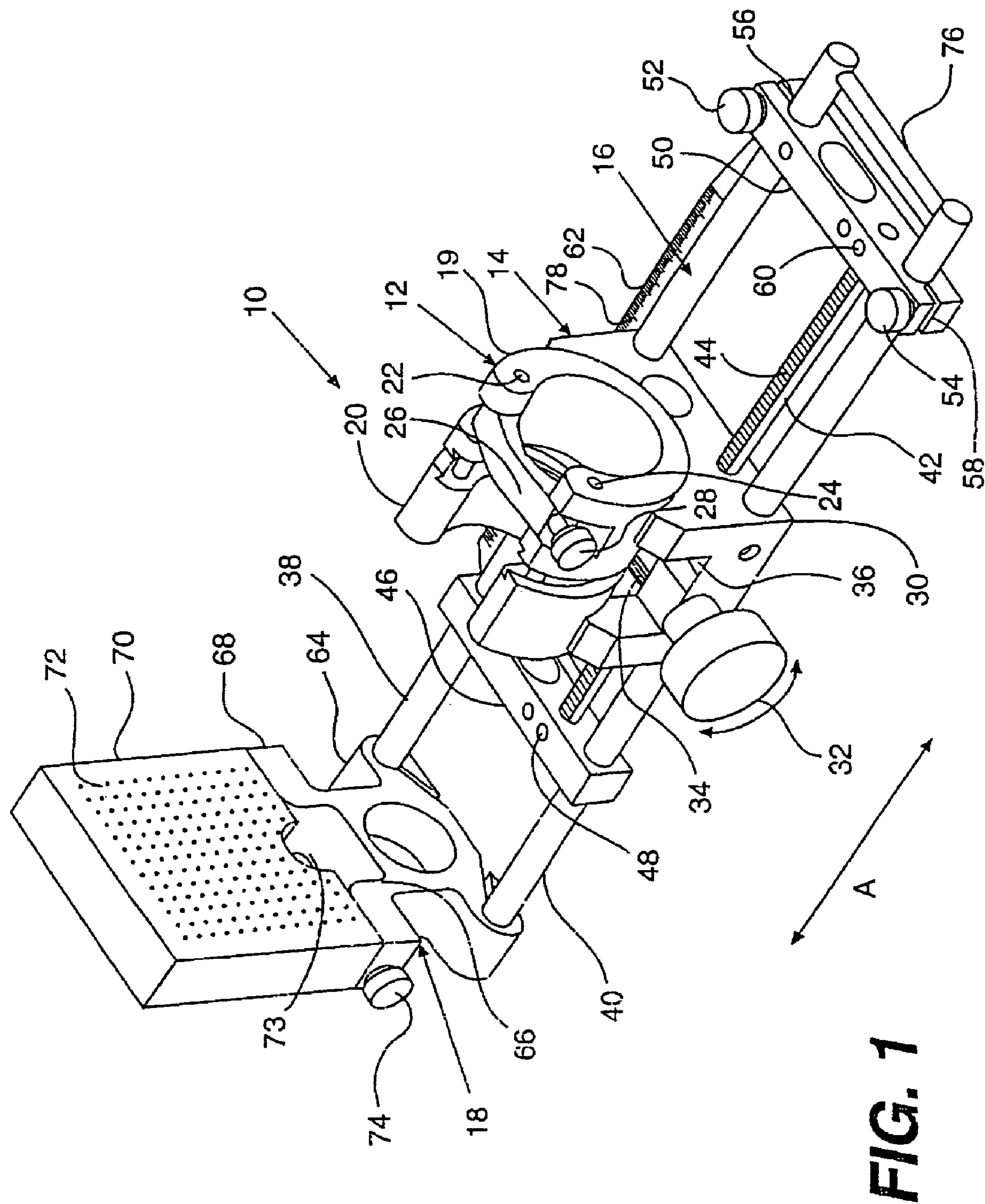
FIG. 1 is a perspective view of one embodiment of the ultrasound probe mount and stepping device according to the present invention, wherein the ultrasound probe mount is in a neutral position.

Referring now to the drawing figures in which like reference designators refer to like elements, there is shown in FIG. 1 the device 10 according to the present invention. The device 10 of the present invention includes an ultrasound probe mount 12, a carriage 14, a base assembly 16, and a template grid mount 18. The probe mount 12 is adapted to receive and securely clamp around a central enlarged portion of an ultrasound probe. This probe mount 12 is held for rotation within carriage 14. The carriage 14 is, in turn, held for slidable longitudinal movement along the base assembly 16 and the template grid mount 18 is adapted to supportively secure a template grid 70 thereatop.

With respect to the rotation and longitudinal motions, the structure, function, and operation of device 10 is analogous to the steppers disclosed in U.S. Pat. No. 5,931,786, the contents of which are incorporated herein by reference.

Figure 2:
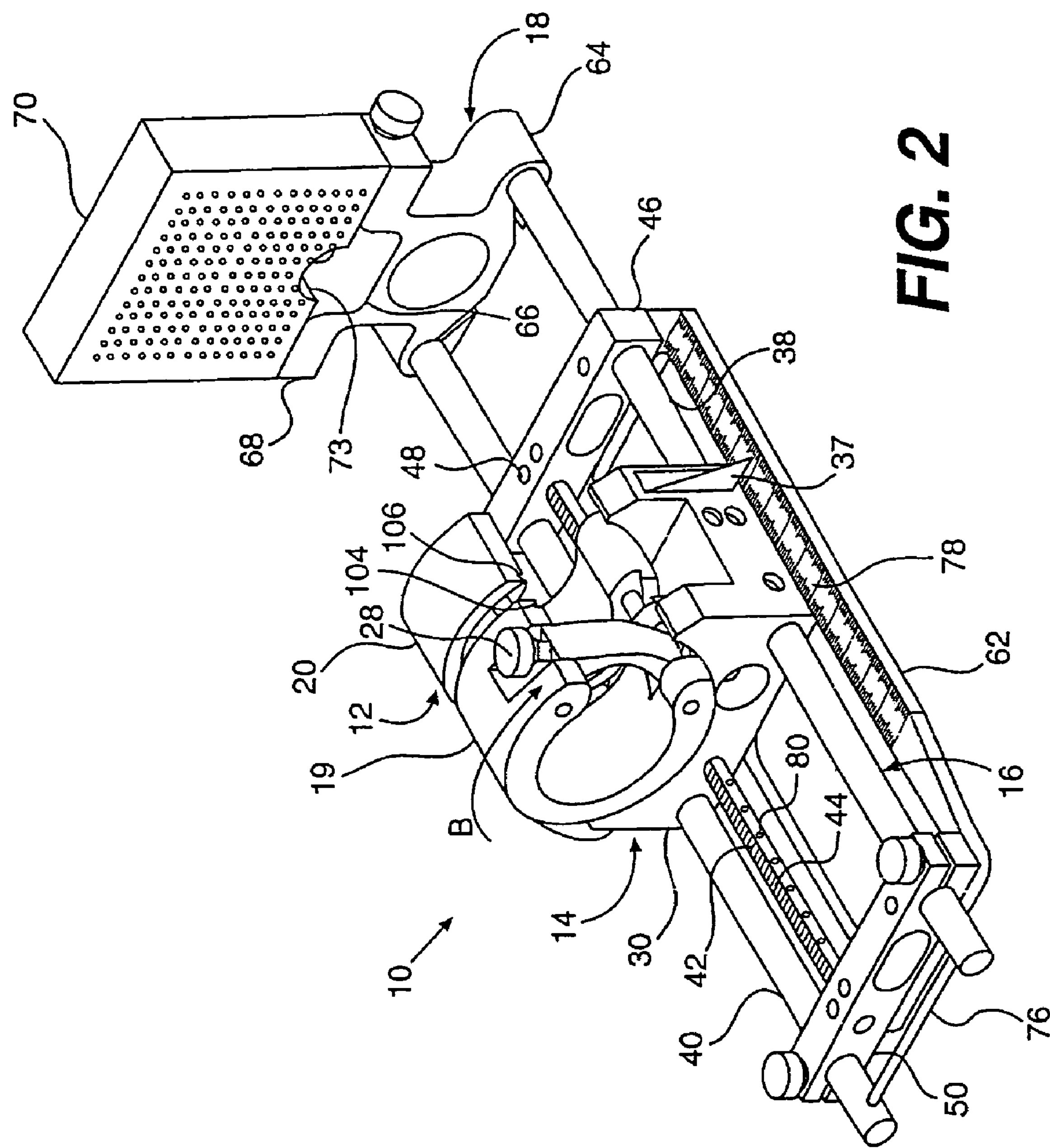
FIG. 2 is a perspective view of the ultrasound probe mount and stepping device of FIG. 1 showing the ultrasound probe mount rotated through 90 degrees clockwise as viewed from the neutral position shown in FIG. 1.
Figure 3:
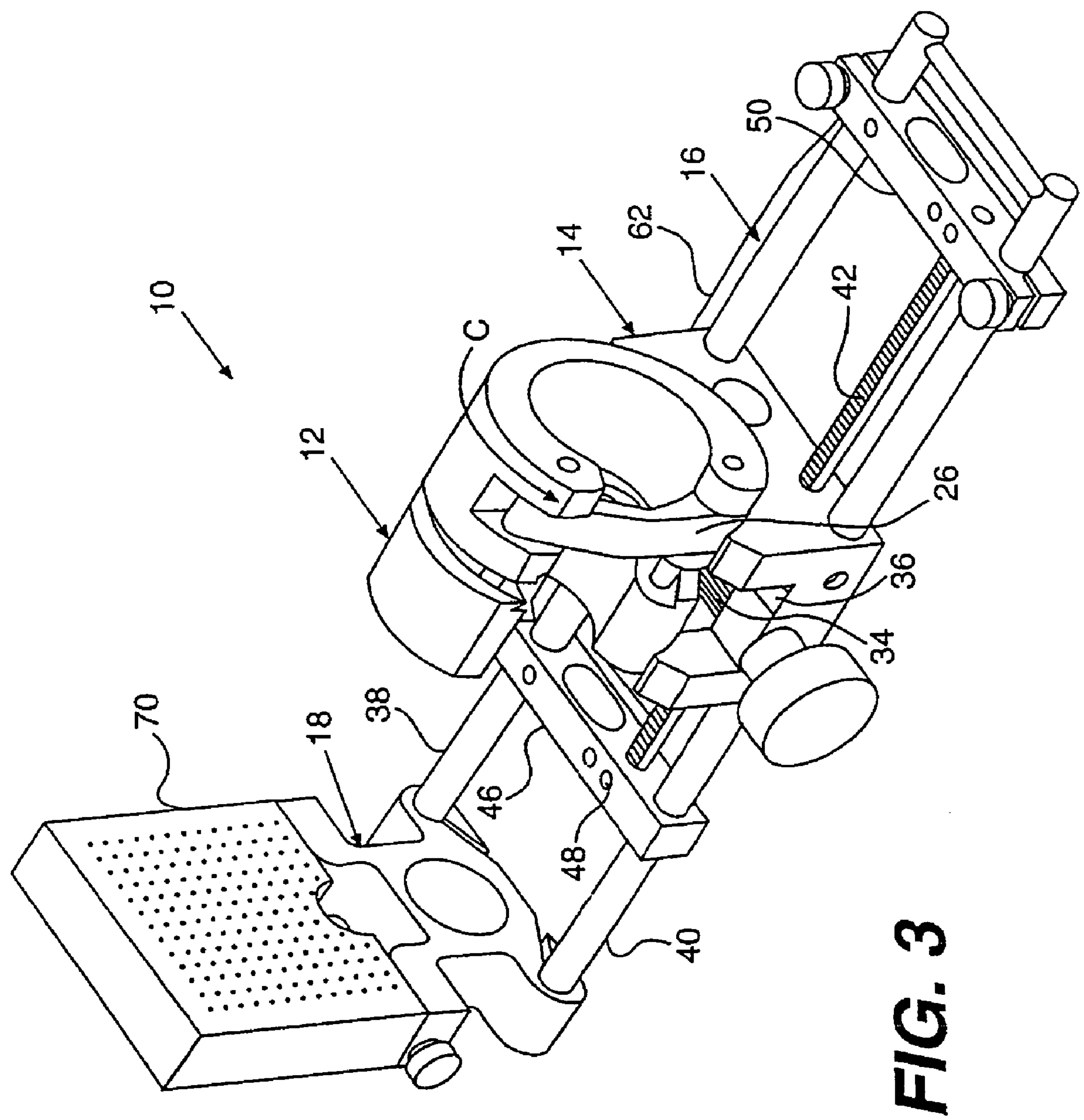
FIG. 3 is a perspective view of the ultrasound probe mount and stepping device of FIG. 1 showing the ultrasound probe mount rotated through about 90 degrees counterclockwise with respect to the neutral position shown in FIG. 1.

With more specific detail of the components of the invention 10 discussed herebelow, and referring additionally to FIGS. 2 and 3, the ultrasound probe mount 12 (with ultrasound probe removed) is manually rotatable against an adjustable friction member back and forth in the direction of arrows B and C through about 90 degrees rotation in either direction from the neutral position of the ultrasound probe mount 12 shown in FIG. 1. As seen in FIG. 3, a cavity 36 is provided as clearance for tightening knob 28 which secures a pivotally connected closure strap 26 for securement of the ultrasound probe therewithin as described more fully herebelow. By this arrangement, the ultrasound probe mount 12 is fully rotatable through about 180 degrees of movement from one extreme to the other. Tightening knob 28, closure strap 26, and probe mount 12 are configured to allow device 10 to be used with ultrasound probes of different sizes, shapes, and manufacture.

The grid mount, as best seen in FIG. 1, is structured for securely clamping and engaging the ends of spaced apart, parallel rails 38 and 40, by lower split flanges 64 which include holes for secure clamping engagement therebetween. The upper flange 68 includes manually tightenable fasteners 74 (typical) on each end thereof for clamping engagement with the template grid 70. A clearance aperture formed by groove 66 in the grid mount 18 and groove 73 formed at the bottom of the template grid 70 provide for clearance access for the elongated sensing portion of the ultrasound probe.

The template grid 70 includes an array of apertures 72 which are precisely arranged and positioned vertically and laterally in a precise manner with respect to the longitudinal axis of the ultrasound probe when it is held within the probe mount 12. These apertures 72 are longitudinally aligned with respect to the device 10 and are sized to receive and precisely align a needle passing therethrough having one or more spaced radioactive pellets held inside the tip of the needle. From the real time ultrasound image produced, in combination with particularly selected apertures 72, a highly accurate placement of the radioactive seeds in the cancerous prostate is achievable.

Figure 4:
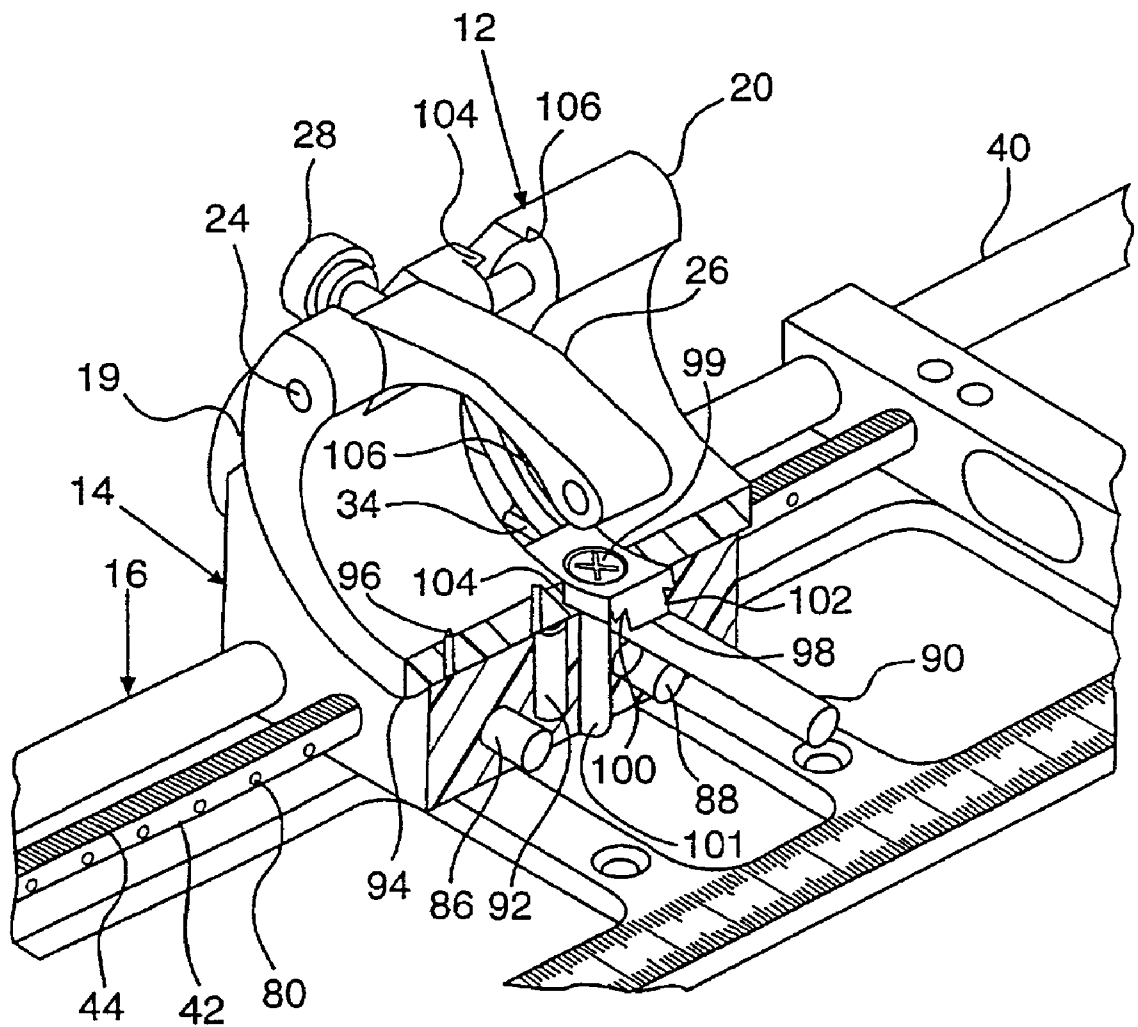
FIG. 4 is an enlarged perspective view in partial section of the ultrasound mount and carriage of the stepper of FIG. 1.
Figure 5:
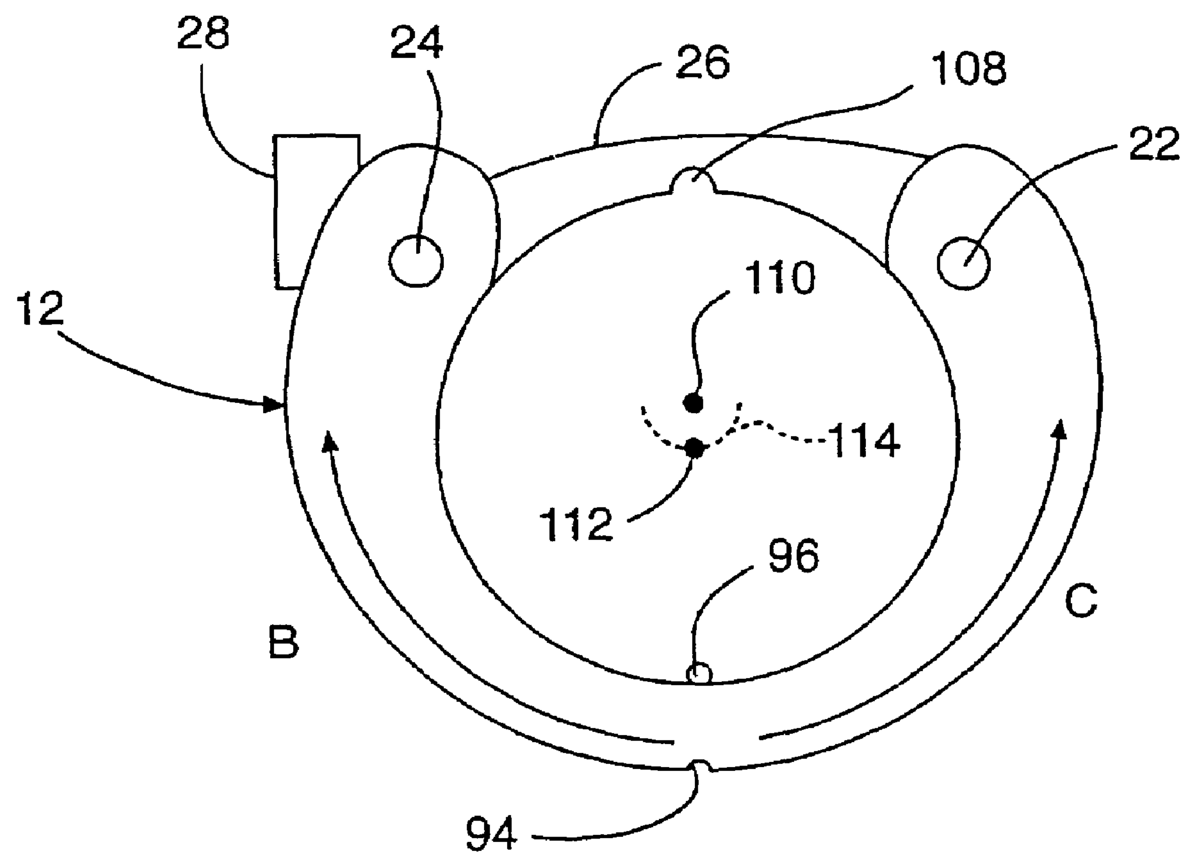
FIG. 5 is an elevation view of one end of the ultrasound probe mount.

Referring now to FIGS. 4 and 5, the details of the probe mount 12, the carriage 14 and the base assembly 16 are shown. The probe mount 12 comprises two generally u-shaped members 19 and 20 which are held spaced apart by longitudinally oriented stainless steel pins 22 and 24. The closure strap 26 is pivotally connected to pin 22, the opposite end of closure strap 26 being structured for locking tightenable engagement by adjusting knob 28 with structure of the corresponding end of u-shaped channel member 19.

The closely spaced facing edges of the u-shaped members 19 and 20 have a dovetail groove 104 and 106 which mateably and trappingly engages with a corresponding dovetail shape of a locking block 98. The locking block 98 is connected to the carriage 14 by a flush mounted threaded fastener 99 which threadably engages into a threaded nylon insert 101 connected within carriage 14 as seen in FIG. 5. The upwardly facing concave contour of locking block 98 generally conforms with the cylindrical aligned inner surfaces of each of the u-shaped members 19 and 20. By this arrangement, the probe mount 12 is rigidly secured within carriage 14 for rotational movement only with the frictional resistance to rotational movement controlled by the tensioning of threaded fastener 99 against locking block 98.

One benefit of this structural arrangement of the probe mount 12 is to allow for at least −90° to +90° movement back and forth in the direction of arrows B and C from a neutral position of the probe mount 12. This neutral position is physically identified by providing a detent ball plunger 92 mounted uprightly within carriage 14 and interacting with a longitudinal groove or other suitable depression 94 formed centrally along the lower outer surface of the probe mount 12. Proper alignment of the ultrasound probe is initially established by providing one or more protuberances 96 which upwardly extend from the inner surface of the u-shaped members 19 and 20. These protuberances 96 interact with a longitudinal groove or other suitable depression formed in most, if not all, ultrasound probe units for identifying a design orientation with respect to the probe mount 12. For probe units having alignment pin(s) rather than a groove or depression, probe mount 12 can be provided with a groove for ensuring alignment.

Referring more specifically to FIG. 5, after the probe is inserted in probe mount 12, the geometric center of the probe is located generally at 112 while the imaging center is located vertically upwardly at 110. In order to compensate for this arrangement, as the probe mount 12 is rotated in the direction of either B or C, the geometric center 112 moves along arc 114 so that imaging center 110 rotates without any lateral displacement.

Another benefit of the structural arrangement of the probe mount 12 and carriage 14 is the ability to remove the probe mount 12 from the carriage 14 by rotation. Because the u-shaped members 19 and 20 do not form a complete circle as shown best in FIGS. 1 and 2, the probe mount 12 can be spun-out or off the carriage 14 until free thereof. This allows for ease of removal of probe mount 12 for cleaning purposes. In addition, this allows the probe mount 12 to be easily replaced with a new unit when inoperative. Such ease of removal and replacement of the probe without loss of position is very desirable during medical procedures should the rectum fill with gas or stool and require cleansing to restore a good ultrasound image.

The base assembly 16 includes two aluminum rails 38 and 40 held in spaced relation at one end by the grid mount 18. The opposite ends of rails 38 and 40 are clampingly engaged into a first transversely oriented crossbar 50 which is clampingly secured by thumb screws 52 and 54 which squeezably engage and reduce the gaps 56 and 58 against the corresponding rails 38 and 40. A separate crossbar 76 is also permanently attached between the corresponding ends of the rails 38 and 40. These crossbars 46 and 50 are connected to and supported by a flat aluminum base plate 62 which is adapted to be secured to a support stand. A preferred support stand for use in this invention is shown in U.S. Pat. No. 5,961,527, the contents of which are incorporated herein by reference. The position of template grid mount 18, and consequently template grid 70, is adjustable by moving rails 38 and 40 using crossbar 76 as a handle when thumbscrews 52 and 54 are loosened. The ability to adjust the position of template grid 70 through the back of device 10 is another benefit.

The carriage 14 is slidably engaged around the rails 38 and 40 through moving longitudinal apertures formed through the lower corners of the carriage 14 as best seen in FIG. 1. Alternatively, a single rail can be used if desired. To control the linear longitudinal movement and secure positioning of the carriage 14 back and forth in the direction of arrow A in FIG. 1, an adjusting knob 32 (on one or both sides of carriage 14) rotatable back and forth in the direction of the arrows is connected to a coaxial gear 34 about a transverse axis with respect to the carriage 14 as also partially seen in FIG. 4. An elongated rack 42 having finely spaced straight teeth 44 formed along one surface thereof is connected at one end to the first crossbar 50. The opposite end of rack 42 is secured within a second transversely oriented crossbar 46. The rack 42 is slidably engageable within a longitudinal aperture formed through carriage 14 and positioned between the longitudinal apertures formed to slidably receive rails 38 and 40.

By this arrangement of gear 34 and stationary rack 44, by rotating the adjusting knob 32 back and forth in the direction of the arrow, movement of the carriage 14 in either direction of arrow A is effected. As best seen in FIGS. 2 and 4, the rack 42 also includes a series of precision spaced laterally facing dimples 80 which interact with spaced spring loaded ball plungers 86 and 88 so as to identify by feel the preselected distance of movement between each felt detent as adjusting knob 32 is rotated to effect movement of the carriage 14. This gear, rack, and detent system achieves the stepping function required during the procedure. An alternative to knowing the exact distance of movement of the carriage 14 is provided by a fixed blade 37 positioned directly above a conventional measuring scale 78 on base plate 62 which can be viewed so as to determine the desired amount of longitudinal movement of the carriage 14.

Figure 6:
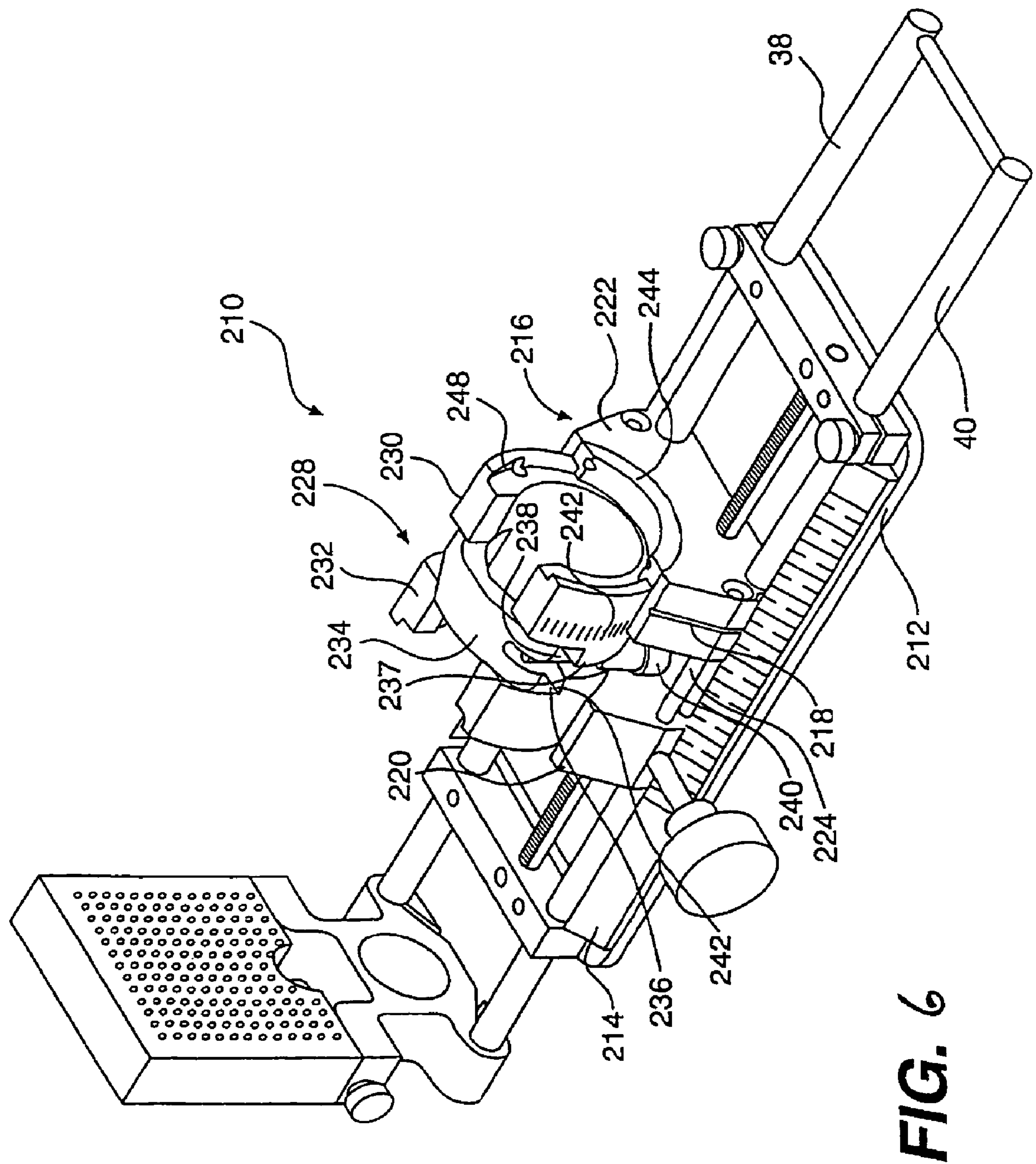
FIG. 6 is a perspective view of another embodiment of the device of the present invention which includes an ultrasound probe mount in a neutral position.
Figure 7:
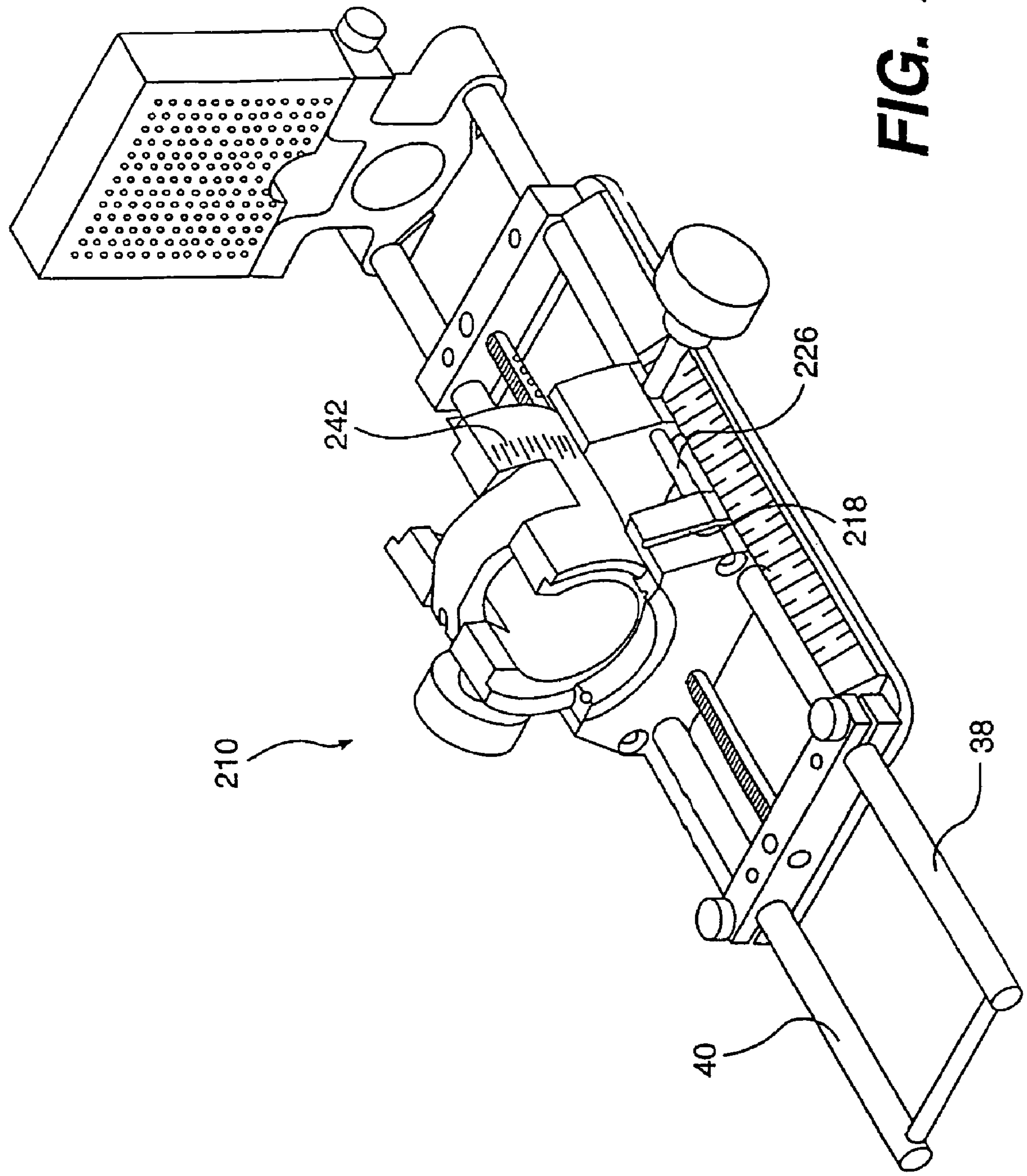
FIG. 7 is a perspective view of the ultrasound probe mount and stepping device of FIG. 6.

Turning now to FIGS. 6 and 7, an alternative embodiment of the device 210 according to the present invention is shown. In general, most of the structure shown in FIGS. 6 and 7 is like or comparable to the structure illustrated in the embodiment shown in previous FIGS. 1 through 5 and accordingly discussion of those like components is not believed necessary. The base plate 212 supports a tilted scale 214 positioned along each elongated side of base plate 212. Preferably the scale 214 is tilted at about forty-five (45) degrees for ease of viewing by the medical personnel using the device of the present invention.

The carriage 216 is formed of two like shaped generally trapezoidal blocks 220 and 222 which are separated and kept apart by pins 224 and 226 as shown in FIGS. 6 and 7. The distance between blocks 220 and 222 is adjustable along pins 224 and 226. Carriage block 220 has an indicator line 218 on each side to match up against the scales 214. As the block moves along rods 38 and 40 the position of the carriage 216 can be measured or determined along either scale 214.

The carriage 216 provides an arcuate recess that accommodates the outer curved portion of a probe mount or cradle 228 which can be formed as an integral piece or bracket with u-shaped members 230 and 232. The closure strap 234 is pinned at one end between unshaped members 230 and 232 for pivotal rotation thereabout. At its other end the closure strap 234 can be positioned within recess 236 defined between u-shaped members 230 and 232. Recess 236 includes a narrow portion 237. A latch pin 238 is rotationally pinned at its one end to the other end of closure strap 234. The other end of latch pin 238 is coupled to tightening knob 240 which can be rotationally threaded on pin 238. After a probe is positioned within probe mount 228, the closure strap 234 can be placed over a portion of the outer surface of the probe. The free or other end of closure strap 234 is placed in the recess 236, the pin 238 is moved into the narrow portion 237 of recess 236, and the tightening knob 240 is rotated on pin 238 to rest against the lower (not shown) shoulders 242 in recess 236. The tightening knob 240 is thus oriented or positioned so that it does not interfere with the top surface of the cradle or probe mount for needle placement nor does it alter the shape of the probe cradle with clamping pressure. Probe mount 228 and in particular tightening knob 240 and closure strap 234 are configured to accommodate various ultrasound probes. The probe mount or cradle 228 also has rotation scales 242 on each side of u-shaped member 230. If desired, rotation scales 242 can also be placed on the other u-shaped member 232.

Figure 8:
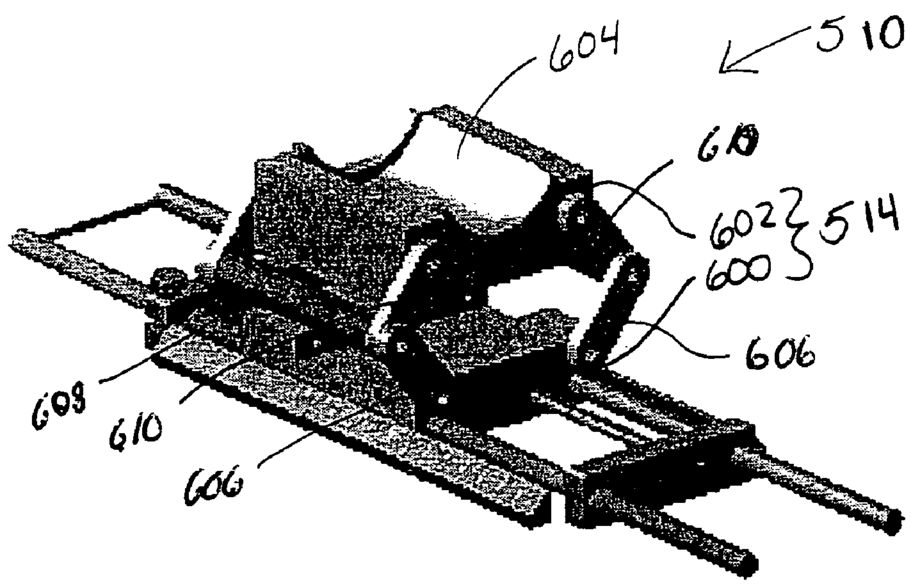
FIG. 8 is a perspective view of another embodiment of an ultrasound probe mount and stepping device according to the present invention with a carriage in a first vertical position.

Although probe mount 228 can be freely positioned in the arcuate recess of carriage 216 for rotational movement about a longitudinal axis of device 210, in one preferred embodiment slotted or grooved guides 244 and 246 are secured by known techniques at upper end portions of carriage 216. The guides 244 and 246 have generally L-shaped cross-sections which fit over corresponding L-shaped grooves 248 in the ends of probe mount 228 which is thus rotationally secured to carriage 216. In this embodiment, the locking block 98 with dovetail grooves 100 and 102 and corresponding mating structures on probe mount 12 are not needed. It is believed that the probe mount 228 is more stably retained in its rotational configuration relative to carriage 216. In addition, because the u-shaped members 230 and 232 do not form a complete circle as shown in FIGS. 7 and 8, the probe mount 228 can be spun-out or off the carriage 216 until free thereof. This allows for ease of removal of probe mount 228 for cleaning purposes. In addition, this allows any broken or worn out probe mount 228 to be easily replaced with a new unit. Such ease of removal and replacement of the probe without loss of position is very desirable during medical procedures should the rectum fill with gas or stool and require cleansing to restore a good ultrasound image.

Figure 9:
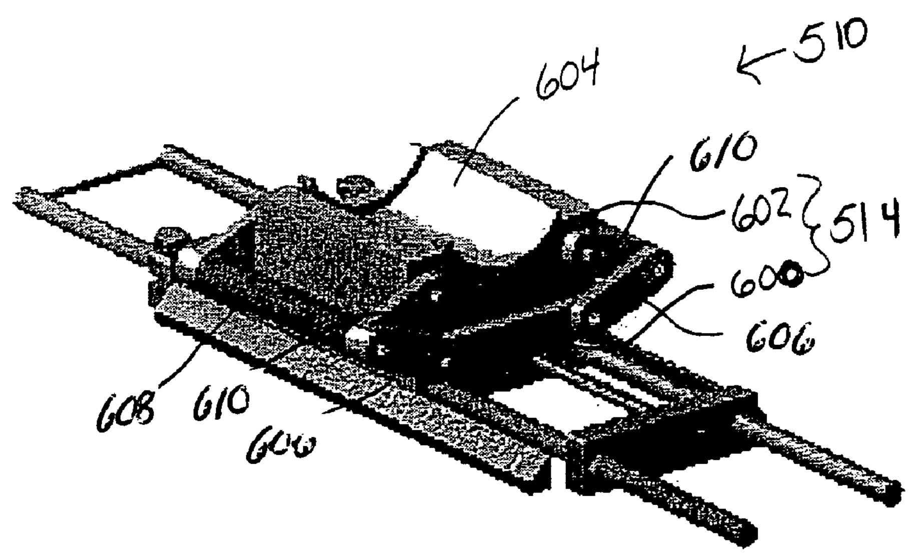
FIG. 9 is a perspective view of the device of FIG. 8 with the carriage in a second vertical position.

FIGS. 8 and 9 show another embodiment of a device 510 according to the present invention. In general, most of the structure shown in FIGS. 8 and 9 is like or comparable to the structure illustrated in the embodiments shown in FIGS. 1-7 and accordingly discussion of those like components is not believed necessary. Unlike carriage 14, a carriage 514 includes a first member 600 and a second member 602. Second member 602 includes a recess 604 for receiving an ultrasound probe. In this regard, second member 602 can be provided with a probe mount analogous to probe mount 12 for securing the ultrasound probe in a manner that allows rotational movement of the probe. First member 600 is coupled to the rest of device 510 in a manner analogous to carriage 14 to provide for controlled longitudinal movement of first member 600.

First and second members 600, 602 are coupled so that the vertical position of second member 602 with respect to first member 600 can be adjusted. Specifically, one end of each of first legs 606 is pivotally connected to first member 600 and the other end of each of first legs 606 is pivotally connected to connecting bars 608 (only one of which is visible in FIGS. 8 and 9). Similarly, one end of each of second legs 610 is pivotally connected to second member 602 and the other end of each of second legs 610 is pivotally connected to connecting bars 608. First and second legs 606, 610 and connecting bars 608 provide a scissor-like mechanism. As a result, second member 602 can be moved up or down with respect to first member 600.

In one embodiment, the operator simply grasps second member 602 or the ultrasound probe, which is fixed with respect to second member 602, to effect the vertical movement. The pivotal connections between first and second legs 606, 610 and connecting bars 608 can be made to have sufficient resistance to maintain the vertical position of second member 602. Alternatively, a locking element, such as a tightening knob located on one of the connecting bars 608, can be provided. In another embodiment, the vertical movement of the second member 602 can be controlled by a worm gear or other mechanism (like that used in an automotive jack) so that more precise movement of second member 602 can be achieved.

Figure 10:
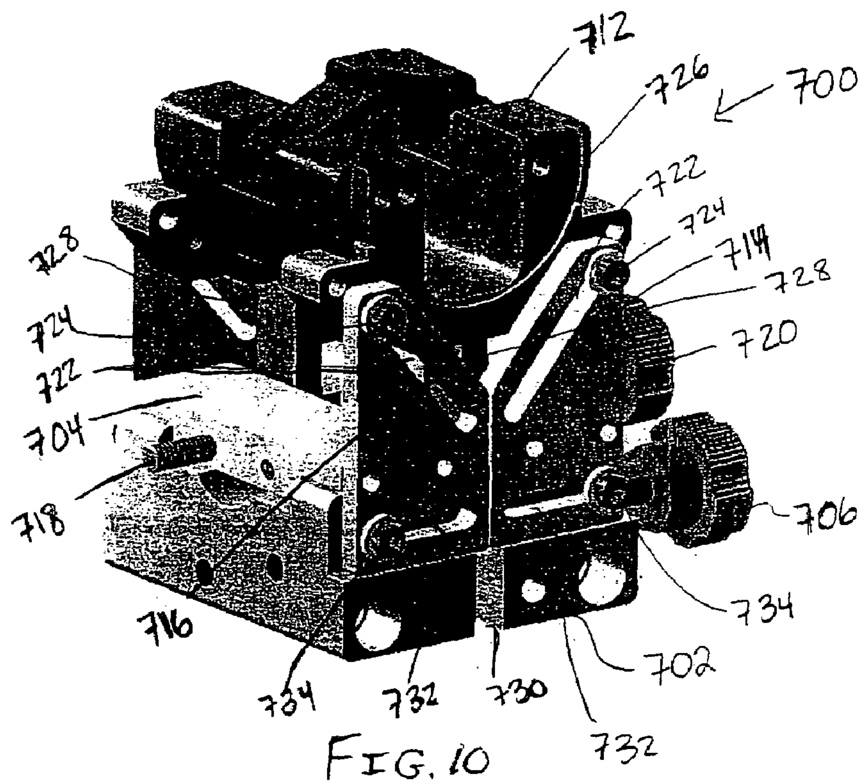
FIG. 10 is a perspective view from one side of another embodiment of a carriage according to the present invention with the carriage in a first vertical position.
Figure 11:
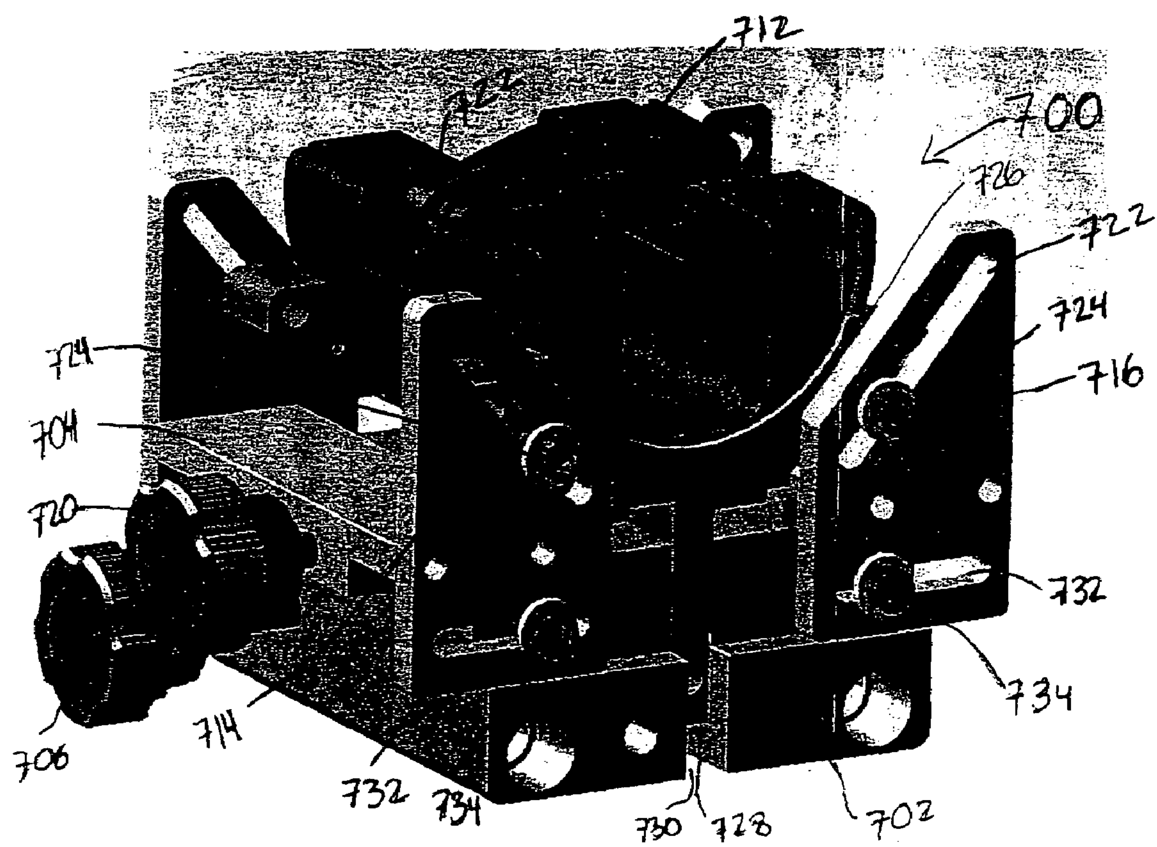
FIG. 11 is a perspective view from another side of the carriage of FIG. 10 with the carriage in a second vertical position.

In this regard, FIGS. 10 and 11 show another embodiment of a carriage 700. The rest of the stepping device is not shown for clarity, but would be analogous to that used with carriage 14, 514. Accordingly, discussion is not believed to be necessary. Carriage 700 includes a first member 702 and a second member 704. First member 702 is coupled to the rest of the stepper in a manner analogous to carriage 14 to provide for controlled longitudinal movement of first member 702 and has a knob 706 for affecting this longitudinal movement. A probe mount 712 analogous to probe mount 12 for securing the ultrasound probe in a manner that allows rotational movement of the probe.

Second member 704 comprises a left housing 714 and a right housing 716. As explained in more detail, left and right housings 714, 716 can move toward and away from each other and are coupled to probe mount 712 so that this movement is translated into vertical movement of probe mount 712. Left and right housings 714, 716 each have a threaded bore for receiving a threaded rod 718 that extends through left and right housings 714, 716. Threaded rod 718 has a vertical control knob 720 at one end. Thus, rotation of knob 720 results in rotation of rod 718. Rotation of knob 720 in one direction causes rod 718 to rotate in the same direction and left and right housings 714, 716 to move toward each other. Rotation of knob 720 in the other direction causes rod 718 to rotate in the same direction and left and right housings 714, 716 to move away from each other.

Each of left and right housings 714, 716 includes an oblique slot 722 in which a bar 724 can travel. Probe mount 712 includes a yoke 726 and each arm of yoke 726 has an aperture through which bar 724 extends. As bars 724 travel in slots 722 (caused by the movement of left and right housings 714, 716 toward or away from each other), yoke 726 is carried with bars 724, thereby resulting in vertical movement of probe mount 712.

Yoke 726 includes one or more fins 728 that move up or down in a groove (or grooves) 730 provided in first member 702. This provides stability to probe mount 712 during vertical movement. Each of left and right housings 714, 716 includes a horizontal slot 732 and first member 702 includes two apertures. A bar 734 extends through each slot 732 and aperture. The cooperation of slots 732, bars 734, and the apertures in first member 702 helps ensure that rotational movement of threaded rod 718 is translated into lateral movement of left and right housings 714, 716. Slots 732 also limit the extent of lateral movement of left and right housings 714, 716. Similarly, slots 722 limit the vertical movement of probe mount 712.

Figure 12:
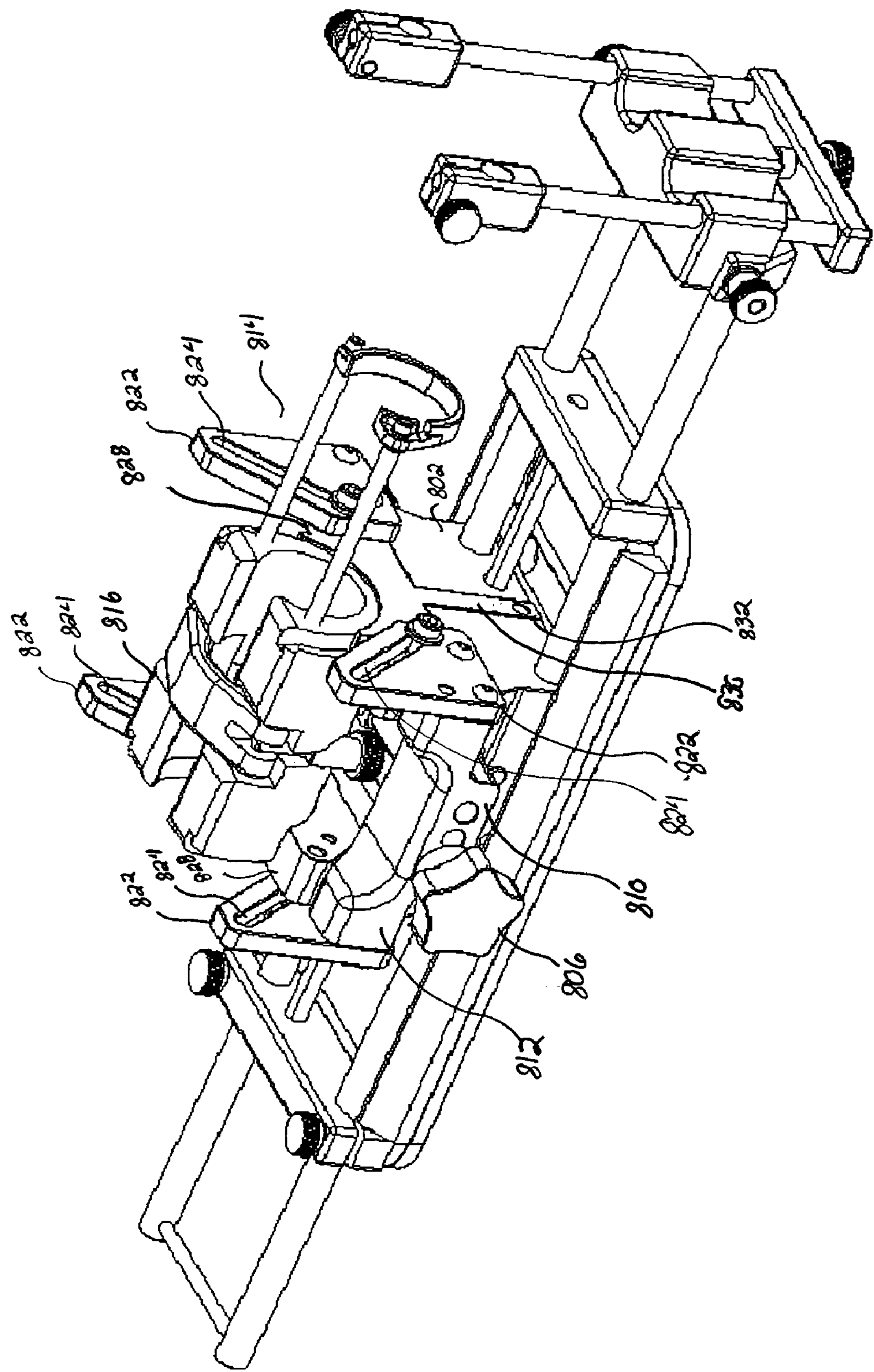
FIG. 12 is a perspective view from one side of another embodiment of a carriage according to the present invention with the carriage in a first vertical position.
Figure 13:
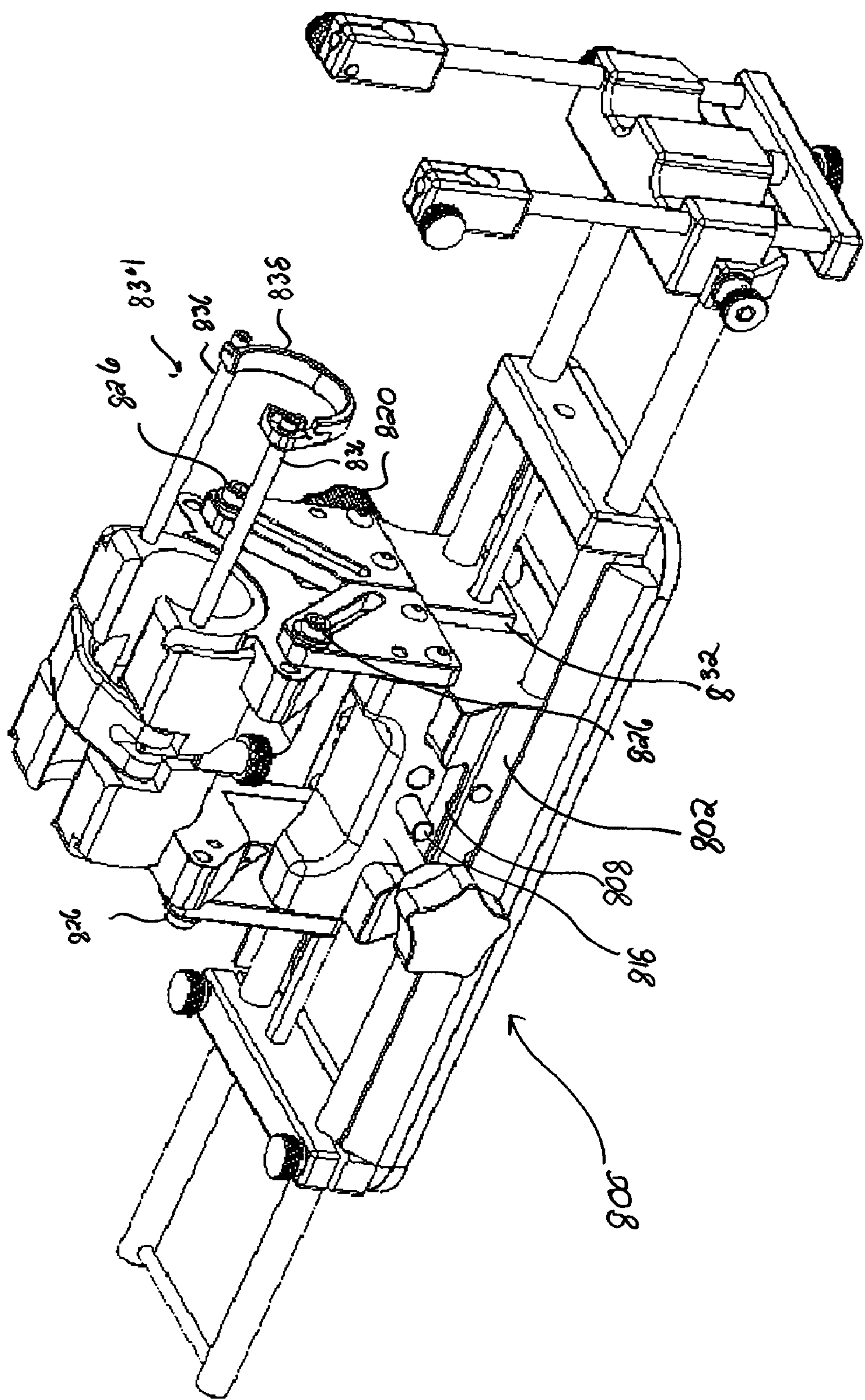
FIG. 13 is a perspective view from another side of the carriage of FIG. 10 with the carriage in a second vertical position

Referring to FIGS. 12 and 13 the carriage 800 includes a first member 802 and a second member 804. First member 802 is coupled to the rest of the stepper in a manner analogous to carriage 14 to provide for controlled longitudinal movement of first member 802 and has a knob 806 for affecting this longitudinal movement. The first member 802 includes a slotted section 808 configured for receiving a top section 810 of the second member 804.

Second member 804 comprises a left housing 812 and a right housing 814. As explained in more detail, left and right housings 812, 814 can move toward and away from each other and are coupled to probe mount 816 so that this movement is translated into vertical movement of probe mount 816. The probe mount 816 is analogous to probe mount 12 for securing the ultrasound probe in a manner that allows rotational movement of the probe.

Left and right housings 812, 814 each have a threaded bore for receiving a threaded rod 818 that extends through left and right housings 812, 814. Threaded rod 818 has a vertical control knob 820 at one end. Thus, rotation of knob 820 results in rotation of rod 818. Rotation of knob 820 in one direction causes rod 818 to rotate in the same direction and left and right housings 812, 814 to move toward each other. Rotation of knob 820 in the other direction causes rod 818 to rotate in the same direction and left and right housings 812, 814 to move away from each other.

Each of left and right housings 812, 812 includes a pair of plate members 822, each having an oblique slot 824 in which a bar 826 can travel. Probe mount 816 includes a yoke 828 and each arm of yoke 828 has an aperture through which bar 826 extends. As bars 826 travel in slots 824 (caused by the movement of left and right housings 812, 814 toward or away from each other), yoke 828 is carried with bars 826, thereby resulting in vertical movement of probe mount 816.

Yoke 828 includes one or more fins 830 that move up or down in a groove (or grooves) 832 provided in first member 802. This provides stability to probe mount 816 during vertical movement.

The probe mount 816 further includes a guide member 834 configured for receiving an ultrasonic probe. The guide member 834 includes a pair of substantially parallel rods 836 extending from the probe mount 816. A probe support 838 is mounted to the distal end of the parallel rods 836, wherein the probe mounted 838 is configured to support a portion of an ultrasonic probe. The guide member 834 assists in maintaining the alignment of the ultrasonic probe as the probe mount 816 is moved in the vertical and horizontal directs.

All of the components of these devices can be made from metal. According to one embodiment, the components can be machined. Alternatively, many of the components can be fabricated or cast of a plastic, with engineering thermoplastics, such as DELRIN, being exemplary. Nylons, polycarbonates and like materials can be used, if desired.

The features of these devices according to the present invention include: lightweight, improving the “feel” and safety when manipulating the probe in the rectum; firm and positive stepping function preventing slippage; easy to read carriage scales; rotational capability of at least 180 degrees with easy to read marking scales from either side; audible and palpable secure centerline detent featuring smooth, clockwise and counterclockwise rotation; grid movement independent of the ultrasound probe controlled from a convenient backside location; standard template grid for needles spaced in 5 mm increments with graphics and elevations specific for each brand of ultrasound (custom grid configurations can also be employed, as desired); and an open configuration and easy separability of components allowing for convenient cleaning and maintenance.

Additionally, the vertical adjustment mechanism allows the operator to pull the ultrasound probe away from the anterior rectal wall (lowering in relation to the template grid) in a controlled and accurate manner. This is performed while keeping the template grid fixed in relation to the patient and after the freezing or heating is completed to accurately return the ultrasound probe to its original position in relation to the template grid and patient. This permits better visualization during the procedure, greater safety, and better control of the therapy being administered.

While various embodiments of the present invention are described above, it should be understood that the various features could be used singly or in any combination thereof. Therefore, this invention is not to be limited to only the specifically preferred embodiments depicted herein.

Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. An apparatus for guiding a medical instrument comprising:

a base assembly;

a carriage assembly slidably mounted to the base assembly and comprising first and second portions moveable in a first plane with respect to each other; and a medical instrument mount mounted to the carriage assembly and having an adjustable vertical height with respect to the base assembly, the medical instrument mount configured and dimensioned for supporting an ultrasound transducer;

wherein the medical instrument mount is moveable in a second plane orthogonal to the first plane;

the carriage assembly comprises a first housing including a pair of substantially parallel first housing plate members and a second housing including a pair of substantially parallel second housing plate members; and the medical instrument mount comprises a yoke member operatively coupled to the first and second housings, such that as the first and second housings are moved in the first plane, the medical instrument mount moves in the second plane orthogonal to the first plane.

2. The apparatus according to claim 1 wherein the carriage assembly comprises a first member slidably mounted to the base assembly and the medical instrument mount comprises a second member.

3. The apparatus according to claim 1 wherein:

the first housing plate members and the second housing plate members each include an oblique slot; and the yoke member includes a plurality of arm members one each slidingly positioned in the oblique slots.

4. The apparatus according to claim 3 wherein the carriage assembly further comprises:

a first member slidably mounted to the base assembly; and a second member operably connected to the first member, the second member being operably connected to the first and second housings.

5. The apparatus according to claim 4 wherein:

the first housing plate members and the second housing plate members each include a horizontal slot; and the second member includes a plurality of arm members one each slidingly positioned in the horizontal slots, such that the first and second housings are slidably connected to the second member.

6. The apparatus according claim 1 wherein the base assembly comprises a base member which is configured and dimensioned for connection to a support stand.

7. The apparatus according to claim 1 further comprising a quick release member operatively associated with the medical instrument mount and carriage assembly for removably attaching and detaching the medical instrument mount to and from the carriage assembly when the carriage assembly is in an imaging position without losing position and orientation of the carriage assembly, wherein the quick release member comprises a grooved portion of the carriage assembly and a tongued portion of the medical instrument mount, the grooved portion configured and dimensioned to receive the tongued portion and the tongued portion releasable from the grooved portion by rotation of the medical instrument mount with respect to the carriage assembly.

8. The apparatus according to claim 1 further comprising first and second elongated, spaced parallel, substantially coextensive rods slidingly mounted to the base assembly, a grid support member adapted to be connected to first ends of the rods, and a handle coupled to second ends of the rods for changing position of the grid support member in relation to the base assembly.

9. The apparatus according to claim 8 further comprising a template grid having a plurality of grid apertures and being removably coupled to the grid support member.

10. The apparatus according to claim 1 further comprising a guide member mounted to the medical instrument mount.

11. An apparatus for guiding a medical instrument comprising:

a base assembly;

a carriage assembly comprising a first member slidably mounted to the base assembly and a second member operably connected to the first member with a scissor-like mechanism, such that the second member has an adjustable height with respect to the first member, the scissor-like mechanism comprising first and second portions moveable in a first plane with respect to each other; and a medical instrument mount mounted to the second member, the medical instrument mount configured and dimensioned for supporting an ultrasound transducer and being movable with the second member, and the medical instrument mount being moveable along a second plane orthogonal to the first plane by the movement of the first and second portions of the scissor-like mechanism;

wherein the scissor-like mechanism includes a plurality of first legs pivotally connected to the first member and a plurality of second legs pivotally connected to the second member, wherein one each of the plurality of first legs is pivotally connected to one each of the plurality of second legs.

12. The apparatus according to claim 11 wherein the pivotal connection between the first and second legs includes at least one connection bar.

13. The apparatus according to claim 12 wherein the connection bar has sufficient resistance to maintain a vertical position of the second member.

14. An apparatus for guiding a medical instrument comprising:

a base assembly;

a carriage assembly including a first member slidably mounted to the base assembly and a second member operably connected to the first member, the second member including a first housing having a pair of substantially parallel first housing plate members and a second housing having a pair of substantially parallel second housing plate members; and a medical instrument mount including a yoke member operably coupled to the first and second housings and being configured and dimensioned for supporting an ultrasound transducer, such that as plate members of the first and second housings are moved in a first plane horizontally with respect to each other, the medical instrument mount moves in a second plane orthogonal to the first plane.

15. The apparatus according to claim 14 wherein:

the first housing plate members and the second housing plate members each include an oblique slot; and the yoke member includes a plurality of arm members one each slidingly positioned in the oblique slots.

16. The apparatus according to claim 15 wherein:

the first housing plate members and the second housing plate members each further include a horizontal slot; and the second member further includes a plurality of arm members one each slidingly positioned in the horizontal slots, such that the first and second housings are slidably connected to the second member.

17. The apparatus according to claim 15 wherein the first and second members each includes a slotted section.

18. The apparatus according to claim 17 wherein the yoke member includes a portion slidably engagable within the slotted section.

19. An apparatus for guiding a medical instrument comprising:

a base assembly comprising a rail member disposed in a longitudinal direction;

a template grid coupled proximate a first end of the base assembly;

a carriage assembly slidably associated with the base assembly and selectively movable in the longitudinal direction, the carriage assembly comprising a first housing including a pair of substantially parallel first housing plate members and a second housing including a pair of substantially parallel second housing plate members; and an ultrasound probe support coupled to the carriage assembly and selectively movable in a direction orthogonal to the longitudinal direction when the first housing plate members and the second housing plate members are moved in a first plane with respect to each other.

* * * * *